(12) United States Patent
Johnsson et al.

(10) Patent No.: US 8,097,239 B2
(45) Date of Patent: Jan. 17, 2012

(54) CONTROLLED-RELEASE FORMULATIONS

(75) Inventors: Markus Johnsson, Lund (SE); Fredrik Tiberg, Lund (SE); Catalin Nistor, Lund (SE)

(73) Assignee: Camurus AB (SE)

( * ) Notice: Subject to any disclaimer, the term of this patent is extended or adjusted under 35 U.S.C. 154(b) by 785 days.

(21) Appl. No.: 11/877,935

(22) Filed: Oct. 24, 2007

(65) Prior Publication Data

US 2008/0124394 A1    May 29, 2008

Related U.S. Application Data

(63) Continuation-in-part of application No. 11/908,740, filed on Feb. 13, 2008.

(30) Foreign Application Priority Data

| Jun. 6, 2005 | (WO) | ................ PCT/GB2005/002217 |
| Dec. 9, 2005 | (WO) | ................ PCT/GB2005/004752 |
| Jun. 6, 2006 | (WO) | ................ PCT/GB2006/002079 |

(51) Int. Cl.
*A61K 49/00* (2006.01)
*A61K 45/00* (2006.01)
*C12P 19/12* (2006.01)

(52) U.S. Cl. ........................ 424/9.2; 424/283.1; 435/100

(58) Field of Classification Search ........................ None
See application file for complete search history.

(56) References Cited

U.S. PATENT DOCUMENTS

| 4,938,763 A | 7/1990 | Dunn et al. |
| 5,480,656 A | 1/1996 | Okada et al. |
| 5,807,573 A * | 9/1998 | Ljusberg-Wahren et al. 424/450 |
| 6,113,943 A * | 9/2000 | Okada et al. ................. 424/457 |
| 6,464,987 B1 * | 10/2002 | Fanara et al. ................. 424/400 |

FOREIGN PATENT DOCUMENTS

| EP | 1 600 162 A1 | 11/2005 |
| WO | WO 03/002136 A | 1/2003 |
| WO | WO 2005/021022 A | 3/2005 |
| WO | WO 2005/046642 A | 5/2005 |
| WO | WO 2005/070394 A | 8/2005 |
| WO | WO 2005/117830 | 12/2005 |

* cited by examiner

*Primary Examiner* — Cecilia J Tsang
*Assistant Examiner* — Satyanarayana Gudibande
(74) *Attorney, Agent, or Firm* — J.A. Lindeman & Co., PLLC (57) ABSTRACT

The present invention relates to formulations of a lipid based controlled-release matrix, a polyhydroxy component and a bioactive agent. Such formulation are useful in the delivery of the bioactive compounds. The invention also relates to the use of a polyhydroxy component for increasing the solubility of a bioactive compound, especially a peptide in a lipid-based controlled-release matrix.

6 Claims, 1 Drawing Sheet

Figure 1. Plasma SOM concentration in rat (n = 6) after subcutaneous administration of a SOM formulation of the invention and a placebo formulation. Error bars denote standard deviation.

SEQUENCE LISTING

<160> NUMBER OF SEQ ID NOS: 4

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

```
-continued

Gln Ala Ala Lys Glu Phe Ile Ala Trp Leu Val Lys Gly Arg Gly
            20                  25                  30

<210> SEQ ID NO 2
<211> LENGTH: 30
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

US 8,097,239 B2

CONTROLLED-RELEASE FORMULATIONS

SEQUENCE LISTING

The present application contains a Sequence Listing, which has been submitted in ASCII format via EFS-Web and is hereby incorporated by reference in its entirety. The ASCII copy, created on Mar. 11, 2011, is named 110005US.txt and is 2,058 bytes in size.

BACKGROUND TO THE INVENTION

The present invention relates to controlled-release lipid composition, and their precursors (pre-formulations). In particular, the invention relates to lipid formulations for the in situ generation of controlled release compositions. Such formulations are low viscosity mixtures (such as molecular solutions) of amphiphilic components for solubilising and releasing at least one bioactive agent. Most specifically, the invention relates to formulations which undergo at least one phase transition upon exposure to aqueous fluids, such as body fluids, thereby forming a controlled release matrix which optionally is bioadhesive.

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable. Furthermore, in some circumstances, such as in the fitting of implants (e.g. joint replacements or oral implants) the area of desired action may not remain accessible for repeated administration. In such cases a single administration must provide active agent at a therapeutic level over the whole period during which activity is needed.

Various methods have been used and proposed for the sustained release of biologically active agents. Such methods include slow-release, orally administered compositions, such as coated tablets, formulations designed for gradual absorption, such as transdermal patches, and slow-release implants such as "sticks" implanted under the skin.

One method by which the gradual release of a bioactive agent has been proposed is a so-called "depot" injection. In this method, a bioactive agent is formulated with carriers providing a gradual release of active agent over a period of a number of hours or days. These are often based upon a degrading matrix which gradually disperses in the body to release the active agent.

The most common of the established methods of depot injection relies upon a polymeric depot system. This is typically a biodegradable polymer such poly (lactic acid) (PLA) and/or poly (lactic-co-glycolic acid) (PLGA) and may be in the form of a solution in an organic solvent, a pre-polymer mixed with an initiator, encapsulated polymer particles or polymer microspheres. The polymer or polymer particles entrap the active agent and are gradually degraded releasing the agent by slow diffusion and/or as the matrix is absorbed. Examples of such systems include those described in U.S. Pat. No. 4,938,763, U.S. Pat. No. 5,480,656 and U.S. Pat. No. 6,113,943 and can result in delivery of active agents over a period of up to several months. These systems do, however, have a number of limitations including the complexity of manufacturing and difficulty in sterilising (especially the microspheres). The local irritation caused by the lactic and/or glycolic acid which is released at the injection site is also a noticeable drawback. There is also often quite a complex procedure to prepare the injection dose from the powder precursor, and this procedure must be conducted at the point of care just prior to administration.

From a drug delivery point of view, polymer depot compositions also have the disadvantage of accepting only relatively low drug loads and having a "burst/lag" release profile. The nature of the polymeric matrix, especially when applied as a solution or pre-polymer, causes an initial burst of drug release when the composition is first administered. This is followed by a period of low release, while the degradation of the matrix begins, followed finally by an increase in the release rate to the desired sustained profile. This burst/lag release profile can cause the in vivo concentration of active agent to burst above the functional window immediately following administration, and then drop back through the bottom of the functional window during the lag period before reaching a sustained functional concentration. Evidently, from a functional and toxicological point of view this burst/lag release profile is undesirable and could be dangerous. It may also limit the equilibrium concentration which can be provided due to the danger of adverse effects at the "peak" point.

A highly effective non-polymeric depot system was disclosed in WO2005/117830, in which a combination of a diacyl lipid or tocopherol, a phospholipid, and an oxygen containing organic solvent are combined to provide a controlled-release matrix. Such a system has considerable advantages, including a transition from low-viscosity to high-viscosity upon exposure to an aqueous environment, and the facility to provide a gradual release of active agent over a long period from a biocompatible and biodegradable composition. The disclosure of this document is hereby incorporated herein by reference.

One limitation of previously know lipid controlled-release formulations is that the solubility of certain active agents, such as peptides and peptide-based compounds is lower than desirable. Although many peptides, proteins and other bioactive agents can effectively be stabilised in the lipid matrices, where the solubility of these is low, then it can be the limiting factor in controlling the duration over which the active agent is released. This is because only a certain volume of composition can be effectively administered without causing unacceptable discomfort to a patient (e.g. 5 ml is a typical maximum desirable volume for sub-cutaneous injection). If the therapeutic window for the active agent requires a high concentration, and/or the active has a short half-life in the system, then the maximum amount of active which can be stabilised in the administration volume will control the maximum duration over which that agent can be released.

The present inventors have now established that by formulating controlled-release lipid matrices with a polyhydroxy component (e.g. a sugar), the level of active agent which may be stabilised in the lipid formulation is considerably enhanced.

BRIEF SUMMARY OF THE INVENTION

In a first aspect, the present invention thus provides a formulation (especially a pharmaceutical formulation) comprising:
i) A lipid based controlled-release matrix
ii) A polyhydroxy component
iii) A bioactive agent.

It is preferable that the components (especially the lipid based controlled-release matrix) will be chosen such that upon contact with aqueous media, the formulation of the invention assembles into an ordered (e.g. non-lamellar) phase structure, such as liquid crystalline phase, $L_2$ (reversed micellar) phase, $L_3$ (sponge) phase, or mixtures thereof.

Generally, the aqueous fluid will be a body fluid such as fluid from a mucosal surface, tears, sweat, saliva, gastrointestinal fluid, extra-vascular fluid, extracellular fluid, interstitial fluid or plasma, and the formulation of the invention will form an ordered phase structure when contacted with a body surface, area or cavity (e.g. in vivo) upon contact with the aqueous body fluid.

In the formulations of the present invention, the lipid based controlled-release matrix will typically comprise suitable lipid, solvent and surfactant components so as to generate the desired phase behaviour.

A suitable controlled-release matrix component (i) comprises a low viscosity mixture of:
a) at least one neutral diacyl lipid and/or a tocopherol;
b) at least one phospholipid;
c) optionally and preferably at least one biocompatible, (preferably oxygen containing) organic solvent;
d) optionally and preferably at least one fragmentation agent.

In the formulation of the invention, the bio active agent (iii) and polyhydroxy component (ii) preferably dissolve or disperse in the lipid matrix component (i) to form a low viscosity mixture.

To the inventor's knowledge, it has never previously been known that the co-formulation of a bioactive agent with a polyhydroxy compound could significantly increase the solubility of the bioactive agent in a lipid matrix.

In a second aspect, the present invention therefore provides the use of a polyhydroxy component to increase the solubility of a bioactive agent in a lipid-based controlled-release formulation. There is furthermore provided, as a third aspect of the invention, a method for increasing the solubility of a bioactive agent in a lipid-based controlled release matrix, said method comprising adding a polyhydroxy component to the bioactive agent and/or to the lipid-based controlled-release matrix.

There is also provided a method of delivery of a bioactive agent to a human or non-human animal (preferably mammalian) body, this method comprising administering (preferably parenterally) a formulation comprising:
i) A lipid based controlled-release matrix
ii) A polyhydroxy component
iii) A bioactive agent.

The method of administration suitable for the above method of the invention will be a method appropriate for the condition to be treated and the bioactive agent used. A parenteral depot will thus be famed by parenteral (e.g. subcutaneous or intramuscular) administration while a bioadhesive non-parenteral (e.g. topical) depot composition may be formed by administration to the surface of skin, mucous membranes and/or nails, to ophthalmological, nasal, oral or internal surfaces or to cavities such as nasal, rectal, vaginal or buccal cavities, the periodontal pocket or cavities formed following extraction of a natural or implanted structure or prior to insertion of an implant (e.g. a joint, stent, cosmetic implant, tooth, tooth filling or other implant).

In a still further aspect the present invention provides a process for the formation of a formulation suitable for the administration of a bioactive agent to a (preferably mammalian) subject, said process comprising dissolving a mixture of a bioactive agent in a lipid-based controlled-release matrix, wherein at least one of said bioactive agent and/or said lipid-based controlled-release matrix is in admixture with a polyhydroxy component.

In a yet still further aspect the present invention provides the use a formulation comprising:
i) A lipid based controlled-release matrix
ii) A polyhydroxy component
iii) A bioactive agent.
in the manufacture of a pre-formulation for use in the sustained administration of said bioactive agent.

BRIEF SUMMARY OF THE FIGURES

In the attached figures.

DETAILED DESCRIPTION OF THE INVENTION

In all aspects of the present invention, the formulations are preferably low viscosity mixtures prior to administration. Herein, the term "low viscosity mixture" is used to indicate a mixture which may be readily administered to a subject and in particular readily administered by means of a standard syringe and needle arrangement. This may be indicated, for example by the ability to be dispensed from a 1 ml disposable syringe through a 22 awg (or a 23 gauge) needle by manual pressure. In a particularly preferred embodiment, the low viscosity mixture should be a mixture capable of passing through a standard sterile filtration membrane such as a 0.22 µm syringe filter. In other preferred embodiments, a similar functional definition of a suitable viscosity can be defined as the viscosity of a pre-formulation that can be sprayed using a compression pump or pressurized spray device using conventional spray equipment. A typical range of suitable viscosities would be, for example, 0.1 to 5000 mPas, preferably 1 to 1000 mPas at 20° C.

It has been observed that by the addition of small amounts of low viscosity solvent, as indicated herein, a very significant change in viscosity can be provided. For example, in some formulations, the addition of only 5% of a suitable solvent can reduce viscosity 100-fold and addition of 10% may reduce the viscosity up to 10,000 fold.

Particularly preferred examples of low viscosity mixtures are molecular solutions and/or isotropic phases such as L2 and/or L3 phases. As describe above, the L3 is a non-lamellar phase of interconnected sheets which has some phase structure but lacks the long-range order of a liquid crystalline phase. Unlike liquid crystalline phases, which are generally highly viscous, L3 phases are of lower viscosity. Obviously, mixtures of L3 phase and molecular solution and/or particles of L3 phase suspended in a bulk molecular solution of one or more components are also suitable. The L2 phase is the so-called "reversed micellar" phase or microemulsion. Most preferred low viscosity mixtures are molecular solutions, L3 phases and mixtures thereof. L2 phases are less preferred, except in the case of swollen $L_2$ phases as described below.

Following exposure to an aqueous environment, it is preferable that the formulations of all aspects of the invention generate bulk or particulate ordered phases. Such phases are generally described herein as "non-lamellar". The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the L3 phase which comprises a multiply interconnected bi-continuous network of bilayer sheets which are non-lamellar but lack the long-range order of the liquid crystalline phases. Depending upon their curvature of the amphiphile sheets, these phases may be described as normal (mean curvature towards the apolar region) or reversed (mean curvature towards the polar region).

The non-lamellar liquid crystalline and L3 phases are thermodynamically stable systems. That is to say, they are not simply a meta-stable state that will separate and/or reform into layers, lamellar phases or the like, but are the stable thermodynamic form of the lipid/solvent mixture. Bulk liquid crystalline phases are highly viscous and are advantageous for the formation of depot compositions wherein controlled release is desired over a prolonged period, especially following parenteral administration. $L_3$ and $L_2$, phases and dispersed particles of non-lamellar phases are typically lower viscosity and more suited to controlled release over shorter time periods, as well as to topical release at body surfaces, both internal and external.

In a particularly preferred embodiment for all aspects of the present invention, a suitable controlled-release matrix component (i) comprises a low viscosity mixture of:
a) at least one neutral diacyl lipid and/or a tocopherol;
b) at least one phospholipid;
c) optionally and preferably at least one biocompatible, (preferably oxygen containing) organic solvent.
d) optionally an preferably at least one fragmentation agent.

Such suitable systems are described in detail in, for example, WO2005/117830 and are demonstrated in the examples included in that publication, which is incorporated herein by reference. In particular, details and proportions of components a), b) and c) correspond to those described below and on pages 9 to 17 of that text.

In this preferred lipid-based controlled-release matrix, weight ratios of components a:b may be anything from 5:95 right up to 95:5. Preferred ratios would generally be from 90:10 to 20:80 and more preferably from 85:15 to 30:70. The most preferred ratios of a:b are close to parity, especially 35:65 to 65:35, more preferably 42:58 to 58:42.

It is preferred that the lipid-based controlled-release matrix forms bulk or particulate ordered phases as described herein.

Component "a" as indicated herein is a neutral lipid component comprising a polar "head" group and also non-polar "tail" groups. Generally the head and tail portions of the lipid will be joined by an ester moiety but this attachment may be by means of an ether, an amide, a carbon-carbon bond or other attachment. Preferred polar head groups are non-ionic and include polyols such as glycerol, diglycerol and sugar moieties (such as inositol and glucosyl based moieties); and esters of polyols, such as acetate or succinate esters. Preferred polar groups are glycerol and diglycerol, especially glycerol.

In one preferred aspect, component a is a diacyl lipid in that it has two non-polar "tail" groups. This is generally preferable to the use of mono-acyl ("lyso") lipids because these are typically less well tolerated in vivo. The two non-polar groups may have the same or a differing number of carbon atoms and may each independently be saturated or unsaturated. Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include caproyl (C6:0), capryloyl (C8:0), capryl (C10:0), lauroyl (C12:0), myristoyl (C14:0), palmitoyl (C16:0), phytanoly (C16:0), palmitolcoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, eaprylic, capric, lauric, myristie, palmitic, phytanic, palmitolic, stearic, oleic, elaidic, linoleic, linolenic, arachidonic, behenic or lignoceric acids, or the corresponding alcohols. Preferable non-polar chains are palmitic, stearic, oleic and linoleic acids, particularly oleic acid.

The diacyl lipid, when used as all or part of component "a", may be synthetic or may be derived from a purified and/or chemically modified natural sources such as vegetable oils. Mixtures of any number of diacyl lipids may be used as component a. Most preferably this component will include at least a portion of diacyl glycerol (DAG), especially glycerol dioleate (GDO). In one favoured embodiment, component a consists of DAGs. These may be a single DAG or a mixture of DAGs. A highly preferred example is DAG comprising at least 50%, preferably at least 80% and even comprising substantially 100% GDO.

An alternative or additional highly preferred class of compounds for use as all or part of component a are tocopherols. As used herein, the term "a tocopherol" is used to indicate the non-ionic lipid tocopherol, often known as vitamin E, and/or any suitable salts and/or analogues thereof. Suitable analogues will be those providing the phase-behaviour, lack of toxicity, and phase change upon exposure to aqueous fluids, which characterise the compositions of the present invention. Such analogues will generally not form liquid crystalline phase structures as a pure compound in water. The most preferred of the tocopherols is tocopherol itself, having the structure below. Evidently, particularly where this is purified from a natural source, there may be a small proportion of non-tocopherol "contaminant" but this will not be sufficient to alter the advantageous phase-behaviour or lack of toxicity. Typically, a tocopherol will contain no more than 10% of non-tocopherol-analogue compounds, preferably no more than 5%© and most preferably no more than 2% by weight.

Tocopherol

In a further advantageous embodiment of the invention, component a) consists essentially of tocopherols, in particular tocopherol as shown above.

A preferred combination of constituents for component a) is a mixture of at least one DAG (e.g. GDO) with at least one tocopherol. Such mixtures include 2:98 to 98:2 by weight tocopherol:GDO, e.g.10:90 to 90:10 tocopherol:GDO and especially 20:80 to 80:20 of these compounds. Similar mixtures of tocopherol with other DAGs are also suitable.

Component "b" in the present invention is at least one phospholipid. As with component a, this component comprises a polar head group and at least one non-polar tail group. The difference between components a and b lies principally in the polar group. The non-polar portions may thus suitably be derived from the fatty acids or corresponding alcohols considered above for component a. It will typically be the case that the phospholipid will contain two non-polar groups, although one or more constituents of this component may have one non-polar moiety. Where more than one non-polar group is present these may be the same or different.

Preferred phospholipid polar "head" groups include phosphatidylcholine, phosphatidylethanolamine, phosphatidylserine and phosphatidylinositol. Most preferred is phosphatidylcholine (PC). In a preferred embodiment, component b) thus consists of at least 50% PC, preferably at least 70% PC and most preferably at least 80% PC. Component b) may consist essentially of PC.

The phospholipid portion, even more suitably than any diacyl lipid portion, may be derived from a natural source. Suitable sources of phospholipids include egg, heart (e.g. bovine), brain, liver (e.g. bovine) and plant sources including soybean. Such sources may provide one or more constituents of component b, which may comprise any mixture of phospholipids.

Since the formulations of the invention are to be administered to a subject for the controlled release of an active agent, it is preferable that the components a and b are biocompatible. In this regard, it is preferable to use, for example, diacyl lipids and phospholipids rather than mono-acyl (lyso) compounds. A notable exception to this is tocopherol, as described above. Although having only one alkyl chain, this is not a "lyso" lipid in the convention sense. The nature of tocopherol as a well tolerated essential vitamin evidently makes it highly biocompatible.

Two particularly preferred combinations of components a and b are GDO with PC and tocopherol with PC, especially in the region 30-90 wt % GDO/tocopherol, 10-60 wt % PC and 1-30% solvent (especially ethanol, n-methylpyrrolidone (NMP) and/or ispropanol).

In addition to amphiphilic components a and b, the pre-formulations of the invention may also contain additional amphiphilic components at relatively low levels. In one embodiment of the invention, the pre-formulation contains up to 10% (by weight of components a and b) of a charged amphiphile, particularly an anionic amphiphile such as a fatty acid. Preferred fatty acids for this purpose include caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable fatty acids are palmitic, stearic, oleic and linoleic acids, particularly oleic acid. It is particularly advantageous that this component be used in combination with a cationic peptide active agent (see below). The combination of an anionic lipid and a cationic peptide is believed to provide a sustained release composition of particular value. This may in part be due to increased protection of the peptide from the degradative enzymes present in vivo.

Optional but preferable component "c" of the lipid-based controlled-release matrix is an oxygen containing organic solvent. Since the formulations are for use in contact with an aqueous fluid, and particularly a body-fluid (e.g. in vivo), it is desirable that this solvent be tolerable to the subject and be capable of mixing with the aqueous fluid, and/or diffusing or dissolving out of the pre-formulation into the aqueous fluid. Solvents having at least moderate water solubility are thus preferred.

Typical solvents suitable for use as component c include at least one solvent selected from alcohols, ketones, esters (including lactones), ethers, amides and sulphoxides. Examples of suitable alcohols include ethanol, isopropanol, benzyl alcohol and glycerol formal. Monools are preferred to diols and polyols. Where diols or polyols are used, this is preferably in combination with an at least equal amount of monool or other preferred solvent. Examples of ketones include acetone, and propylene carbonate. Suitable ethers include diethylether, glycofurol, diethylene glycol monoethyl ether, dimethylisobarbide, and polyethylene glycols. Suitable esters include ethyl acetate, benzyl benzoate and isopropyl acetate and dimethyl sulphide is as suitable sulphide solvent. Suitable amides include NMP, 2-pyrrolidone, and dimethylacetamide (DMA), and sulphoxides include dimethylsulphoxide (DMSO). Less preferred solvents include dimethyl isosorbide, tetrahydrofurfuryl alcohol, diglyme and ethyl lactate.

The solvent component c will generally be at least partially lost upon in vivo formation of the depot composition, will evaporate, or will be diluted by absorption of water from the surrounding air and/or tissue. It is preferable, therefore, that component c be at least to some extent water miscible or dispersible, and at least should not repel water to the extent that water absorption is prevented. In this respect also, oxygen containing solvents with relatively small numbers of carbon atoms (for example up to 10 carbons, preferably up to 8 carbons) are preferred. Obviously, where more oxygens are present a solvent will tend to remain soluble in water with a larger number of carbon atoms. The carbon to heteroatom (e.g. N, O, preferably oxygen) ratio will thus often be around 1:1 to 6:1, preferably 2:1 to 4:1. Where a solvent with a ratio outside one of these preferred ranges is used then this will preferably be no more than 75%, preferably no more than 50%, in combination with a preferred solvent (such as ethanol). This may be used, for example to decrease the rate of evaporation of the solvent from the pre-formulation in order to control the rate of liquid crystalline depot formation.

The amount of component c, where present in the formulations of the invention and in the lipid-based controlled-release matrix will be at least sufficient to provide a low viscosity mixture (e.g. a molecular solution, see above) of all, and will be easily determined for any particular combination of components by standard methods. The phase behaviour itself may be analysed by techniques such as visual observation in combination with polarized light microscopy, nuclear magnetic resonance, and cryo-transmission electron microscopy (cryo-TEM) to look for solutions, L2 or L3 phases, or liquid crystalline phases. Viscosity may be measured directly by standard means. As described above, an appropriate practical viscosity is that which can effectively be syringed and particularly sterile filtered. This will be assessed easily as indicated herein. The maximum amount of component c to be included will depend upon the exact application of the formulation but generally the desired properties will be provided by any amount forming a low viscosity mixture (e.g. a molecular solution, see above) and/or a solution with sufficiently low viscosity. Since the administration of unnecessarily large amounts of solvent to a subject is generally undesirable the amount of component c will typically be limited to no more than ten times (e.g. three times) the minimum amount required to form a low viscosity mixture, preferably no more than five times and most preferably no more than twice this amount. The composition of the present invention may, however, contain a greater quantity of solvent than would be acceptable in an immediate dosage composition. This is because the process by which the active agents are slowly released (e.g. formation of shells of liquid crystalline phase se described herein) also serve to retard the passage of solvent from the composition. As a result, the solvent is released over some time (e.g. minutes or hours) rather than instantaneously and so can be better tolerated by the body.

Since viscosity is a highly significant factor in administering compositions by injection or spraying, it is preferred that the solvent be itself of very low viscosity. The viscosity of the "low viscosity" solvent component c (single solvent or mixture) should typically be no more than 18 mPas at 20° C. This is preferably no more than 15 mPas, more preferably no more than 10 mPas and most preferably no more than 7 mPas at 20° C. Furthermore, the solvent should be suitable for lowering the viscosity of the matrix, polyhydroxy compound and active agent mixture, since the polyhydroxy compound tends to increase the inherent viscosity of the lipid-based matrix. Ethanol is particularly preferred as suitable in all of these respects. Higher proportions of solvent may also be used for non-parenteral (e.g. topical) applications, especially to body surfaces, where the solvent will be lost by evaporation rather than absorbed into the body. For such applications up to 100 times the minimum amount of solvent may be used (e.g. up to 95% by weight of the composition, preferably up to 80% by weight and more preferably up to 50% by weight), especially where a very thin layer of the resulting non-parenteral depot is desired.

As a general guide, the weight of component c will typically be around 0.5 to 50% of the total weight of the a-b-c (and d where present) solution. This proportion is preferably (especially for injectable depots) 2 to 30% and more preferably 5 to 20% by weight.

The pre-formulations of the present invention typically do not contain significant amounts of water. Since it is essentially impossible to remove every trace of water from a lipid composition, this is to be taken as indicating that only such minimal trace of water exists as cannot readily be removed. Such an amount will generally be less than 1% by weight, preferably less that 0.5% by the weight of the pre-formulation. In one preferred aspect, the pre-formulations of the invention do not contain glycerol, ethylene glycol or propylene glycol and contain no more than a trace of water, as just described.

As optional but preferably fragmentation agent component d) can function any amphiphile capable of serving as a fragmentation agent with the selected components a) and b) (and c) where present). A fragmentation agent is a (pure or mixed) agent which allows the composition comprising components a) and b) to form (by self-dispersion or by the input of energy, such as by shearing or sonication) structured particles, as described herein. Particularly suitable particles are e.g. nonlamellar, especially liquid crystalline, $L_2$ or $L_3$.

There are a number of different molecular classes that are suitable as fragmentation agents in the present invention. These include;
1) Polymeric agents: Poloxamers (preferably Pluronic® F127, Pluronic® F68, Pluronic® F108 Pluronic® L44), 2-Methacryloyloxyethyl phosphorylcholine n-butyl methacrylate co-block polymers (such as PUREBRIGHT MB-37-50T and PUREBRIGHT MB-37-100T from NOF Corp.), pegylated sorbitan fatty acid esters (polysorbates, particularly Polysorbate 80), PEGylated surfactants (e.g. Solutol HS15 from BASF), pegylated castor oil derivatives (e.g. Cremophor EL, Cremophor RH40), pegylated fatty acids (e.g. PEG-oleate), pegylated phospholipids (including DOPE-PEG(2000), DOPE-PEG(5000) and DSPE-PEG(5000)), polyglycerin(PG)-phospholipids (such as DSPE-PG, for example, SUNBRIGHT DSPE-PG8G from NOF Corp., DOPE-PG), pegylated oligoalkylsorbitols (such as PEG-60 Sorbitoltetraoleate, e.g. GO-460V from Nikko Chemicals), pegylated glyceryl fatty acid esters (e.g. TMGO-15 (Nikko Chemicals)), pegylated tocopherols such as d-alpha tocopheryl polyethylene glycol 1000 succinate (Vitamin E TPGS (Eastman)) and pegylated alkyl ethers;
2) Polyol surfactants: sugar derived alkyl esters (such as sucrose laurate and sucrose oleate), sugar derived alkyl ethers (e.g. octyl glucoside);
3) Proteins: including casein, sodium caseinate, lysozyme;
4) Anionic surfactants: Carboxylates of fatty acids (especially sodium oleate, sodium palmitate, sodium stearate, sodium myristate), alkyl sulfates (such as sodium dodecyl sulphate (SDS)); and
5) Cationic surfactants: alkyl ammonium salts (including dodecyl trimethyl ammonium bromide (DTAB), cetyl trimethyl ammonium bromide (CTAB) and oleyl ammonium chloride).

Generally, in the present invention, protein fragmentation agents, such as those described in 3) above are less preferred.

The majority of the d)-components form normal micellar (L1) phases on contact with excess water. However, the components need not form micelles to function as fragmentation agents. The effective functioning of a fragmentation agent will easily be tested by a skilled worker by preparing appropriate compositions and conducting simple tests as illustrated in the Examples herein, and also by reference to WO2006/013369 (particularly the Examples), the disclosure of which is incorporated herein by reference.

Where component d) is present, the components a), b) and d) will typically be present in the following proportions (where a, b and d are the weights of components a), b) and d) respectively); d/(a+b+d) is between 0.01 and 0.3. Compositions within this range have a high tendency to self-disperse or to form stable particles following dispersion with or without energy input. It is preferred, especially where it is desired to provide self-dispersion and greatest particle size control that the proportions of a), b) and d) are such that a/(a+d) is between 0.25 (e.g. 0.35) and 0.80 (e.g. 0.75), more preferably 0.35 (e.g. 0.4) and 0.75 (e.g. 0.65) and d/(a+b+d) is between 0.03 and 0.25 (e.g. 0.2) (where a, b and d are the weights of components a), b) and d) respectively).

A key aspect of the present invention is that the inventors have established a way in which a greater proportion of active agent may be incorporated into a lipid-based controlled-release matrix than would be possible with previous formulations. They have established that the inclusion of a polyhydroxy component (ii) can dramatically increase the quantity of bioactive agent which can be successfully stabilised in the lipid matrix.

The nature of the polyhydroxy component is primarily that it is made up of at least one small organic molecule (e.g. molecular weight 100 to 1000 amu, preferably 150 to 700 amu, most preferably 160 to 360 amu) with at least 4 hydroxy groups. Preferably the polyhydroxy compounds will have 4 to 40 hydroxy groups, preferably 5 to 20 hydroxy groups, and more preferably 5 to 15 hydroxy groups. Sugars or sugar derivatives are preferred polyhydroxy groups, and mono-, di-, and tri-saccharides (especially disaccharides) are particularly preferred. Most preferred examples are trehalose and sucrose.

The amount of polyhydroxy component required in the formulation or the suitability of any particular polyhydroxy compound or mixture will be dependent upon the nature of the lipid component i), the nature of the bioactive agent iii), the inherent solubility of the bioactive agent in the lipid part, and the concentration which is required in order to achieve sufficient loading of the active agent in the administration volume. In any particular case, the suitability and/or required amount may easily be established by formulation of the composition using required components (i) and (iii), both alone and with increasing proportions of polyhydroxy component ii) and observing whether the active agent forms a stable formulation. Suitable procedures are described in detail in the attached Examples.

As a guide, typical weight ratios of polyhydroxy component to bioactive agent (that is to say components ii) iii)) will be 50:1 to 1:5, more preferably 20:1 to 1:2, and most preferably 10:1 to 1:1.

The formulations of the present invention contain a bioactive agent component iii) (described equivalently as "active agents" herein). Active agents may be any compound having a desired biological or physiological effect, such as a protein, drug, antigen, nutrient, cosmetic, fragrance, flavouring, diagnostic, pharmaceutical, vitamin, or dietary agent and will be formulated at a level sufficient to provide an in situ concentration at a functional level (including local concentrations for topical compositions). Under some circumstances one or more of components a, b and/or c may also be an active agent, although it is preferred that the active agent should not be one of these components. Most preferred active agents are pharmaceutical agents including drugs, vaccines, and diagnostic agents.

It has been particularly observed by the present inventors that polymeric biomolecules such as peptide and peptide-based (e.g. protein) active agents achieve a considerable enhancement in their ability to be stably incorporated into lipid matrix systems by inclusion of a polyhydroxy component according to the present invention. Favoured biological active materials therefore comprise amino acids, oligo- and poly-peptides, proteins, oligonucleotides, vaccines, as well as analogs, derivatives and mimetics thereof.

Examples of peptide-based active agents of particular suitability include peptide hormones (e.g. amine derived hormones, peptide hormones, and polypeptide hormones), enzymes (e.g. oxidoreductases, transferases, hydrolases, lyases, ligases), proteins (e.g. albumins, apoproteins, blood proteins, cytosceletal proteins, DNA-binding proteins, fetal proteins, pungal proteins, aprotinin, globulins, heat-shock proteins, hemeproteins, lectins, blood proteins, membrane proteins, metalloproteins, mithochondrial proteins, neoplasm proteins, nerve tissue proteins, nuclear proteins, nucleoproteins, carrier proteins, plant proteins, recombinant proteins, scleroproteins, serpins, transcription factors, viral proteins, contractile proteins), biological factors and products (e.g. antitoxins, biological markers, chemotactic markers, coagulase, toxins, antitoxins, immune sera, vaccines), antibodies (e.g. monoclonal, polyclonal), antibody fragments (e.g. Fab, F(ab)$_2$, and seVF), antigens (e.g. viral antigens, allergens), cytokines (e.g. lymphokines, immunotoxins).

Specific examples of suitable active materials include Erythropoetin (epoetin Alpha, epoetin beta, darbepoetin alpha), G-CSF (Filgrastim), insulin (including analogs and derivatives, mimetics), somatropin (hGH), interferons (including interferon alpha, interferon beta, and analogs), interleukins (including IL-1, IL-2, IL-3, ... IL-33), glucagon-like peptide-1 (and glucagon-like peptide-1 receptor agonists), glucagon-like peptide-2 (and glucagon-like peptide-2 receptor agonists), somatostatin and somatostatin analogues, melanocyte-stimulating hormones and their related peptides, adrenocorticotropic hormone (ACTH) and its fragments, angiotensin and its related peptides, antibodies and their fragments, antigens and their fragments, atrial natriuretic peptides, bioadhesive peptides, bradykinins and their related peptides, calcitonins and their related peptides, cell surface receptor protein fragments, chemotactic peptides, cyclosporins, cytokines, dynorphins and their related peptides, endorphins and P-lidotropin fragments, enkephalin and their related proteins, enzyme inhibitors, immunostimulating peptides and polyaminoacids, fibronectin fragments and their related peptides, gastrointestinal peptides, gonadotropin-releasing hormone (GnRH) agonists and antagonist, growth hormone releasing peptides, immunostimulating peptides, luthenizing hormone releasing hormones (LHRH) and their related peptides, nuclear localization signal related peptides, neurotensins and their related peptides, neurotransmitter peptides, opioid peptides, oxytocins, vasopressins and their related peptides, parathyroid hormone and its fragments, protein kinases and their related peptides, substance P and its related peptides, transforming growth factors (TGF) and their related peptides, tumor necrosis factor fragments, toxins and toxoids and functional peptides such as anticancer peptides including angiostatins, antihypertension peptides, anti-blood clotting peptides, and antimicrobial peptides; selected from the group consisting of proteins such as immunoglobulins, angiogenins, bone morphogenic proteins, chemokines, colony stimulating factors (CSF), cytokines, growth factors, leptins, leukaemia inhibitory factors, stem cell factors and transforming growth factors.

Of particular suitability for the present inventions are interferons (including analogues, such as IFNAR receptor complex binders), glucagon-like peptide-1 receptor agonists, glucagon-like peptide-2 receptor agonists, somatostatin and somatostatin analogues.

Interferons (IFNs) are a family of naturally occurring proteins, which have molecular weights ranging from 15,000 to 21,000 daltons, produced by nucleated cells, molecules that have anti-viral, anti-proliferative, and immune-regulating activity. Interferrons include Types I, II and III, of which Type I includes all alpha and beta (plus omega, epsilon, and kappa) interferons as well as analogues including all IFNAR receptor complex binders. Some examples of suitable therapeutic interferons and analogues (and corresponding products) include; Alpha-2a (Roferon-A), Alpha-2b (Intron-A), Alpha-n3 (Alferon), Alfacon-1 (Infergen), Peginterferon alfa-2a (Pegasys), Peginterferon alfa-2b (Peg-Intron), Beta-1a (Rebif, Avonex), Beta-1b (Betaseron). Known Type II interferons include interferon gamma, and Type III consist of interferon lambda.

Glucagon-like peptide (GLP)-1 is a potent glucoregulatory hoiinone that is released from intestinal L cells into the circulation in response to nutrient ingestion and neural and endocrine stimuli. Structurally, GLP-1 precursor (precursor to the active forms) is a 37-amino acid peptide with a MW of 4.2 KDa, having a sequence highly conserved between different species. After post-translational cleavage of the first six amino acids of the precursor, two equipotent active forms of GLP-1 ((7-37) and (7-36)amide) are generated. GLP-1 is involved in modification of glucose homeostasis through actions that include potentiation of glucose-stimulated insulin secretion and biosynthesis and suppression of glucagon secretion, gastric emptying, and food intake. The therapeutic potential of native GLP-1 is limited by its very short plasma half-life (below 2 minutes). This is due to both rapid inactivation by the proteolytic enzyme dipeptidyl peptidase (DPP)-IV and renal clearance. Consequently, long-acting, DPP-IV-resistant GLP-1 analogues have been developed for clinical use, including exenatide (Byetta, Amylin-Lilly), liraglutide (Novo Nordisk), CJC-1131 (ConjuChem), AVE010 (Zealand Pharma-Sanofi-Aventis), LY548806 (Lilly), TH-0318 (TheraTechnologies), BIM 51077 (Ipsen-Roche). All these are once- or twice-daily administration products; a controlled-release (one week) exenatide product (Exenatide LAR Alkermes-Amylin-Lilly) is currently under clinical investigation. These GLP-1 mimetics bind to GLP-1 receptors with similar or higher affinity and produce biological actions identical to those of native GLP-1 but are resistant to DPP-IV-mediated inactivation and renal clearance.

The structures and sequences of the two equipotent naturally occurring forms of GLP-I and some known analogues are shown below. A straightforward system is used to describe fragments and analogues of GLP-I. For example, Arg34-GLP-I(7-37) designates an analogue of GLP-I formally derived from GLP-I precursor by deleting the amino acid residues Nos. 1 to 6 and substituting the naturally occurring amino acid residue in position 34 (Lys) by Arg.

```
                                            SEQ ID NO. 1
Native (human) GLP-1(7-37):
His7-Ala-Glu-Gly10-Thr-Phe-Thr-Ser-Asp15-Val-Ser-
Ser-Tyr-Leu20-Glu-Gly-Gln-Ala-Ala25-Lys-Glu-Phe-
Ile-Ala30-Trp-Leu-Val-Lys-Gly-Arg-Gly37

SEQ ID NO. 2
Native (human): GLP-1(7-36)amide
```

Other suitable GLP-1 receptor aganists are described in e.g. Knudsen et al. J. Med. Chem. 2000, 43, 1664-1669; Knudsen J. Med. Chem. 2004, 47, 4128-4134; Hui et al. Diabetes Metab. Res. Rev. 2005, 21, 313-331 and Holz and Chepumy Curr. Med. Chem. 2003, 10, 2471-2483. These citations are incorporated herein by reference in their entireties, and although specific passages are referred to herein, all GLP-1 analogue sequences and all GLP-1 receptor agonists referred to in any of these documents are suitable for use in the present invention. GLP-1 receptor agonists as referred to herein includes all GLP-1 analogues as described above and in the references cited above.

Since GLP-1 is a peptide hormone, typical GLP-1 analogues and receptor agonists will be peptides, especially of around 30 amino acids, e.g. 20 to 45, especially 25 to 38. Preferably such peptides will be structurally related to GLP-1 and/or one or more of the known analogues, including those listed here. Peptides may contain only amino acids selected from those 20 α-amino acids indicated in the genetic code, or more preferably may contain their isomers and other natural and non-natural amino acids, (generally α, β or γ amino acids) and their analogues and derivatives.

Amino acid derivatives are especially useful at the termini of the peptides, where the terminal amino or carboxylate group may be substituted by or with any other functional group such as hydroxy, alkoxy, carboxy, ester, amide, thio, amido, amino, alkyl amino, di- or tri-alkyl amino, alkyl (by which is meant, herein throughout C1-C12 alkyl, preferably C1-C6 alkyl e.g. methyl, ethyl, n-propyl, isopropyl, n-butyl, iso-, sec- or t-butyl etc.), aryl (e.g. phenyl, benzyl, napthyl etc) or other functional groups, preferably with at least one heteroatom and preferably having no more than 10 atoms in total, more preferably no more than 6.

By "GLP-1 analogue", as used herein is indicated any GLP-1 receptor agonist (or less preferably antagonist), including naturally occurring forms of GLP-1, either human or from any other species. These analogues are preferably peptides, peptide derivatives or peptide mimics. Peptide derived GLP-1 agonists are most preferred, such as those indicated above and especially GLP-1(7-37), GLP-1(7-36) amide, Liraglutide, AVE-010 (ZP10), TH0318 and Exenatide.

Glucagon like peptide-2 receptor agonists correspond in nature to the active agents described above for GLP-1 receptor agonists, but are active against the GLP-2 receptor.

In one aspect, the active agent is not GLP-1. In a related aspect, the active agent is not a GLP-1 analogue or GLP-1 receptor agonist. These are described in detail above.

Somatostatin is a 14 residue cyclic peptide hormone having the sequence Ala-Gly-Cys-Lys-Asn-Phe-Phe-Trp-Lys-Thr-Phe-Thr-Ser-Cys, where the two cystine residues are connected by a disulphide bridge to generate a type II β-turn at the key binding sequence of Phe-Trp-Lys-Thr. Somatostatin is a natural peptide hormone also known as Growth Hormone Release Inhibiting Factor and has a role as an antagonist of insulin, glucogen and certain other hormones in the release of somatotrophin (Human Growth Hormone). The biological half-life of natural Somatostatin is very short (1-3 minutes) and so it is difficult to generate a viable therapeutic formulation using this active, but an increasing number of somatostatin analogues are becoming available with higher activities and/or longer clearance times in vivo.

Somatostatin analogues, such as octreotide, lanreotide, vapreotide and related peptides, are used or indicated in the treatment of a variety of conditions where they are typically administered over an extended period. Preferred somatostatin analogues are peptide analogues including those comprising modified amino acids such as those described above in relation to other actives.

The amount of bioactive agent to be formulated with the pre-formulations of the present invention will depend upon the functional dose and the period during which the depot composition formed upon administration is to provide sustained release. Typically, the dose formulated for a particular agent will be around the equivalent of the normal daily dose multiplied by the number of days the formulation is to provide release. Although the rate of release from a lipid-based controlled-release matrix can be highly linear, the highest concentration will generally be shortly after administration and the dose will need to be tailored to take into account any adverse effects of a relatively high dose at the beginning of treatment. The precise amount suitable in any case will readily be determined by suitable experimentation.

As a working guide, a level of 1 mg to 200 mg of active agent per 1 g of lipid-based controlled-release matrix is a suitable level. This will more preferably be 2 to 100 mg of active agent per gram of matrix. An administration volume of 0.05 to 10 ml, preferably 0.1 to 8 ml (especially 0.2 to 5 ml) is highly appropriate, especially for parenteral application, to balance drug-loading, ease of administration and discomfort to the subject.

In one embodiment, the pre-formulations of the present invention will generally be administered parenterally. This administration will generally not be an intra-vascular method but will preferably be subcutaneous, intracavitary, intravitreal or intramuscular. Typically the administration will be by injection, which term is used herein to indicate any method in which the formulation is passed through the skin or other body surface, such as by needle, catheter or needle-less injector. Subcutaneous, intracavitary, intravitreal or intramuscular injection by any suitable method will thus be appropriate.

In an alternative embodiment, the formulations of the present invention may form non-parenteral depots where the active agent is slowly released at a body surface. It is especially important in this embodiment that the pre-formulations of the invention and/or the liquid crystalline depot compositions formed therefrom should preferably be bioadhesive. That is to say that the compositions should coat the surface to which they are applied and/or upon which they form as appropriate and should remain even when this surface is subject to a flow of air or liquid and/or rubbing. It is particularly preferable that the liquid crystalline depot compositions formed should be stable to rinsing with water. For example, a small volume of depot precursor may be applied to a body surface and be exposed to a flow of five hundred times its own volume of water per minute for 5 minutes. After this treatment, the composition can be considered bioadhesive if less than 50% of the bioactive agent has been lost. Preferably this level of loss will be matched when water equaling 1000 times and more preferably 10 000 times the volume of the composition is flowed past per minute for five, or preferably 10, minutes.

Although the non-parenteral depot compositions of the present invention may absorb some or all of the water needed to form a liquid crystalline phase structure from the biological surfaces with which they are contacted, some additional water may also be absorbed from the surrounding air. In particular, where a thin layer of high surface area is formed then the affinity of the composition for water may be sufficient for it to form a liquid crystalline phase structure by contact with the water in the air. The "aqueous fluid" referred to herein is thus, at least partially, air containing some moisture in this embodiment.

Non-parenteral depot compositions will typically be generated by applying the pre-formulation topically to a body surface or to a natural or artificially generated body cavity and/or to the surface of an implant. This application may be by direct application of liquid such as by spraying, dipping, rinsing, application from a pad or ball roller, intra-cavity injection (e.g to an open cavity with or without the use of a needle), painting, dropping (especially into the eyes) and similar methods. A highly effective method is aerosol or pump spraying and evidently this requires that the viscosity of the pre-formulation be as low as possible and is thus highly suited to the compositions of the invention. Non-parenteral depots may, however, be used to administer systemic agents e.g. transmucosally or transdermally.

Non-parenteral depots may also be used for application to surfaces, particularly of implants and materials which will be in contact with the body or a body part or fluid. Devices such as implants, catheters etc. may thus be treated e.g. by dipping or spraying with the preformulations of the invention, which will form a robust layer to reduce the introduction of infection. Anti-infective actives are particularly suited to this aspect.

Non-parenteral depot compositions are also of significant benefit in combination with non-pharmaceutical active agents, such as cosmetic actives, fragrances, essential oils etc. Such non-pharmaceutical depots will maintain the important aspects of bioadhesion and sustained release to provide prolonged cosmetic effects, but may easily be applied by spraying or wiping. This additionally applies to agents which have both cosmetic and medical (especially prophylactic) benefits such as sun-protective agents. Since the topical depot compositions provide robust, water resistant barriers which can solubilise high levels of actives, they are especially suitable for sunscreens and sunblocks in combination with ultra violet light (UV, e.g. UVa, UVb and/or UVc) absorbing and/or scattering agents, particularly where high levels of protection is desirable. The compositions are furthermore highly biocompatible and may act to moisten and soothe the skin during sun exposure. Compositions of the invention containing soothing agents such as aloe vera are also highly suitable for soothing and moistening application after exposure to sunlight, or to skin which is dry, inflamed or damaged due to, for example irritation, burning or abrasion.

The formulations of the present invention preferably provide structured phases such as non-lamellar liquid crystalline depot compositions upon exposure to aqueous fluids, especially in vivo and in contact with body surfaces. As used herein, the term "non-lamellar" is used to indicate a normal or reversed liquid crystalline phase (such as a cubic or hexagonal phase) or the L3 phase or any combination thereof. The term liquid crystalline indicates all hexagonal, all cubic liquid crystalline phases and/or all mixtures thereof. Hexagonal as used herein indicates "normal" or "reversed" hexagonal (preferably reversed) and "cubic" indicates any cubic liquid crystalline phase unless specified otherwise. By use of the pre-formulations of the present invention it is possible to generate any phase structure present in the phase-diagram of components a and b with water. This is because the pre-formulations can be generated with a wider range of relative component concentrations than previous lipid depot systems without risking phase separation or resulting in highly viscous solutions for injection. In particular, the present invention provides for the use of phospholipid concentrations above 50% relative to the total amphiphile content. This allows access to phases only seen at high phospholipid concentrations, particularly the hexagonal liquid crystalline phases, and also is highly effective in solubilising the polyhydroxy/active agent components.

A very considerable advantage of the present invention is that formulations having a high loading of bioactive agent are stable in a form suitable for direct administration. That is to say, the formulations require no preparation at the point of care, but may be pre-generated on a large scale and distributed in ready-to-administer form. This is made still more beneficial because each of the components is a simple liquid or soluble component which may be sterilised by filtration or by heat-treatment using routine methods. All the formulations, in all aspects of the invention are therefore preferably in a ready-to-administer form. The formulations may thus be distributed in single-dose or multiple-dose sterile packages ready for immediate use. Such distribution might conveniently be in the form or a pre-loaded administration device.

In a further aspect, the invention therefore provides a pre-loaded administration device containing a formulation as described herein. Preferably, the device will contain a single or multiple doses of the formulation. Preferably the device and formulation will be sterile and sterile-packed. Preferably the formulation will be ready-to-administer.

Similarly, the invention provides in a further aspect a kit comprising one or more measured doses of a formulation of the invention, as described here, and at least one administration device.

Suitable administration devices will depend upon the nature and use of the particular composition, but may be, for example syringes (which may be provided with or without needles), needle-less injectors, sprays, aerosols, injection pens and so forth.

The invention will now be further described by reference to the following, non-limiting, examples:

EXAMPLES

Abbreviations Used:

| Name | Abbreviation | Supplier |
| --- | --- | --- |
| Phosphatidylcholine, soy | SPC | Lipoid, Germany |
| Dioleoyl phosphatidylcholine (synthetic) | DOPC | Lipoid, Germany |
| Glycerol dioleate | GDO | Danisco, Denmark |
| Ethanol (99.5%) | EtOH | Kemetyl, Sweden |
| Trehalose | TRE | Sigma-Aldrich, Sweden |
| Sucrose | SUC | Sigma-Aldrich, Sweden |
| Mannitol | MAN | Sigma-Aldrich, Sweden |
| Peroxidase (horseradish) | PER | Sigma-Aldrich, Sweden |
| Pepsin | PEP | Sigma-Aldrich, Sweden |
| Lysozyme | LYS | Sigma-Aldrich, Sweden |
| Glucagon-like peptide 1 (7-36)amide, acetate salt | GLP-1 | PolyPeptide Laboratories, Inc., CA, USA |
| Somatostatin, acetate salt | SOM | PolyPeptide Laboratories, Inc., CA, USA |

Example 1

Preparation of Liquid Non-Aqueous Lipid Formulations of Pepsin (PEP)

Liquid lipid formulations of SPC/GDO/EtOH or DOPC/GDO/EtOH were prepared by weighing in the respective component in a glass vial followed by end-over-end rotation for at least 6 h at RT. The lipid compositions used are indicated in Table 1.

TABLE 1

Lipid compositions in weight % (wt %)

| Lipid formulation # | SPC | DOPC | GDO | EtOH |
| --- | --- | --- | --- | --- |
| 1 | 45 | — | 45 | 10 |
| 2 | 42.5 | — | 42.5 | 15 |
| 3 | — | 42.5 | 42.5 | 15 |

Aqueous solutions of PEP (MW ca 35 kDa) were prepared by dissolving PEP in an aqueous solution containing the required amount of polyhydroxy-component (TRE, SUC or MAN, where present) in glass vials. The final PEP concentration was 10 mg/mL. The resulting solutions were frozen at −85° C. for 1 h followed by freeze-drying overnight. The resulting powders comprising PEP/polyhydroxy-component in weight ratios from 2:1 to 1:3 were finely grounded using a spatula before addition to the lipid formulations.

Each of the formulations was tested for ability to generate a homogenous formulation with PEP in the absence of any polyhydroxy compound. Under all conditions investigated, PEP could not be dissolved to any visually observable degree in any of the lipid formulations 1-3.

The freeze-dried powders were added to the lipid formulations such that the final PEP concentration in the formulations was 1 wt % followed by end-over-end rotation for 1-3 days. The resulting formulations were then visually assessed for homogeneity and transparency where a homogenous and transparent sample indicates complete PEP dissolution. The results are given in Table 2.

TABLE 2

Lipid/PEP/polyhydroxy-component formulations (lipid composition as in Table 1)

| Lipid formulation # | PEP/TRE (wt:wt) | PEP/SUC (wt:wt) | PEP/MAN (wt:wt) | Homogenous and transparent formulation | PEP conc. (wt %) |
| --- | --- | --- | --- | --- | --- |
| 1 | 1:1 | — | — | YES | 1 |
| 1 | 1:2 | — | — | YES | 1 |
| 1 | 1:2.5 | — | — | YES | 1 |
| 1 | 1:3 | — | — | YES | 1 |
| 2 | 1:2.5 | — | — | YES | 1 |
| 3 | 1:2.5 | — | — | YES | 1 |
| 2 | — | 1:2.5 | — | YES | 1 |
| 1 | — | — | 1:2.5 | NO | 1 |

It is clear from the results in Table 2 that TRE and SUC give high solubility enhancing effects in the non-aqueous lipid matrix whereas MAN is not effective.

Example 2

Preparation of Liquid Non-Aqueous Lipid Formulations of Lysozyme (LYS)

Liquid lipid formulations were prepared as described in Example 1.

Freeze-dried powders of LYS (MW ca 15 kDa) and polyhydroxy-component were prepared in the same way as for PEP in Example 1.

LYS was again tested for solubility in the matrix as a pure compound. As with PEP, pure LYS could not be dissolved to any visually observable degree in any of the lipid formulations 1-3.

The freeze-dried powders were added to the lipid formulations such that the final LYS concentration in the formulations was 1-2 wt % followed by end-over-end rotation for 1-3 days. The resulting formulations were then visually assessed for homogeneity and transparency where a homogenous and transparent sample indicates complete LYS dissolution. The results are given in Table 3.

TABLE 3

Lipid/LYS/polyhydroxy-component formulations (lipid composition as in Table 1)

| Lipid formulation # | LYS/TRE (wt:wt) | LYS/MAN (wt:wt) | Homogenous and transparent formulation | LYS conc. (wt %) |
| --- | --- | --- | --- | --- |
| 1 | 1:2.5 | — | YES | 1 |
| 2 | 1:2.5 | — | YES | 1 |
| 3 | 1:2.5 | — | YES | 2 |
| 2 | — | 1:2.5 | NO | 1 |

It is clear from the results in Table 3 that TRE gives a high solubility enhancing effect in the non-aqueous lipid matrix whereas MAN is not effective.

Example 3

Preparation of Liquid Non-Aqueous Lipid Formulation of Peroxidase (PER) from Horseradish Liquid lipid formulations were prepared as described in Example 1.

Freeze-dried powders of PER (MW ca 40 kDa) and polyhydroxy-component were prepared in the same way as for PEP in Example 1.

PER was tested for solubility in the matrix as a pure compound. As with PEP and LYS, pure PER could not be dissolved to any visually observable degree in any of the tested lipid formulation (formulation 2).

The freeze-dried powders were added to the lipid formulations such that the final PER concentration in the formulations was 1 wt % followed by end-over-end rotation for 4 hours. The resulting formulations were then visually assessed for homogeneity and transparency where a homogenous and transparent sample indicates complete PER dissolution. The results are given in Table 4.

TABLE 4

Lipid/PER/polyhydroxy-component formulation
(lipid composition as in Table 1)

| Lipid formulation # | PER/TRE (wt:wt) | Homogenous and transparent formulation | PER conc. (wt %) |
|---|---|---|---|
| 2 | 1:2.5 | YES | 1 |

It is clear from the results in Table 4 that TRE gives a high solubility enhancing effect in the non-aqueous lipid matrix.

Example 4

Preparation of Liquid Non-Aqueous Lipid Formulation of Somatostatin (SOM)

Liquid lipid formulations were prepared as described in Example 1.

Freeze-dried powders of SOM (MW ca 1.6 kDa) and polyhydroxy-component were prepared in the same way as for PEP in Example 1.

The freeze-dried powders were added to the lipid formulations such that the final SOM (free base) concentration in the formulations was 1-2 wt % followed by end-over-end rotation for 1-3 days. The resulting formulations were then visually assessed for homogeneity and transparency where a homogenous and transparent sample indicates complete SOM dissolution. The results are given in Table 5.

TABLE 5

Lipid/SOM/polyhydroxy-component formulation
(lipid composition as in Table 1)

| Lipid formulation # | SOM/TRE (wt:wt) | Homogenous and transparent formulation | SOM (free base) conc. (wt %) |
|---|---|---|---|
| 1 | 1:2.5 | YES | 1 |
| 2 | 1:2.5 | YES | 2 |
| 3 | 1:2.5 | YES | 2 |

It is clear from the results in Table 5 that TRE gives a high solubility enhancing effect in the non-aqueous lipid matrix yielding SOM (free base) concentrations of at least 2 wt %. For pure SOM, a substantial amount of non-dissolved SOM was still present in the samples after more than 3 days equilibration at RT.

Example 5

Preparation of Liquid Non-Aqueous Lipid Formulation of Glucagon-Like Peptide 1 (GLP-1)

Liquid lipid formulations were prepared as described in Example 1.

Freeze-dried powders of GLP-1 (MW ca 3.3 kDa) and polyhydroxy-component were prepared in the same way as for PEP in Example 1 except that 0.1 wt % acetic acid was included in the aqueous medium before freeze-drying.

The freeze-dried powders were added to the lipid formulations such that the final GLP-1 concentration in the formulations was 1-1.5 wt % followed by end-over-end rotation for 1-3 days. The resulting formulations were then visually assessed for homogeneity and transparency where a homogenous and transparent sample indicates complete GLP-1 dissolution. The results are given in Table 6.

TABLE 6

Lipid/GLP-1/polyhydroxy-component formulation
(lipid composition as in Table 1)

| Lipid formulation # | GLP-1/TRE (wt:wt) | GLP-1/MAN (wt:wt) | Homogenous and transparent formulation | GLP-1 conc. (wt %) |
|---|---|---|---|---|
| 1 | 1:1 | — | YES | 1 |
| 1 | 1:2 | — | YES | 1 |
| 1 | 1:2.5 | — | YES | 1 |
| 2 | 1:2.5 | — | YES | 1 |
| 2 | — | 1:2.5 | NO | 1 |
| 3 | 1:2.5 | — | YES | 1.5 |

It is clear from the results in Table 6 that TRE gives a high solubility enhancing effect in the non-aqueous lipid matrix whereas MAN is not effective. Importantly, for pure GLP-1, a substantial amount of non-dissolved GLP-1 was still present in the samples after more than 3 days equilibration at RT.

Example 6

Measurement of Residual Peroxidase Activity in Horseradish Peroxidase (PER) Based Lipid Formulations A liquid lipid formulation comprising 0.95 wt % PER (9.53 mg PER/g) and a lipid composition of SPC/GDO/EtOH=42.5/42.5/15 wt % was prepared as described in Example 3.

The resulting homogenous and transparent formulation was tested for peroxidase activity in the following way:

The lipid sample was weighed directly in a 2 mL volumetric flask and then dissolved and filled to volume with a mixture of methanol (MeOH) and dimethyl sulphoxide (DMSO) at a 1:1 volume ratio.

5.70 mg of tetramethyl benzidine (TMB) was dissolved in 950 pt DMSO. 400 μL of the resulting solution were mixed with 12 mL citrate buffer (50 mM, pH 5.5) also containing 13.5 μL $H_2O_2$ 30% (substrate mixture). 50 μL standards of samples were dispensed in duplicate in separate wells of a transparent microtiter plate, and mixed with 150 μL/well substrate mixture. After incubation for 15 mM at room temperature (dark), the reaction was stopped with 100 μL/well 2N HCl. The absorbance at 450 nm in each well was recorded.

The peroxidase activity (equivalents PER, mg/g) in the three replicates of the lipid formulation is presented in Table 7 below.

TABLE 7

Peroxidase activity in the lipid formulation.
Three replicates were measured.

| Replicate | Equivalents PER, mg/g | CV, % | Recovery, % |
|---|---|---|---|
| I | 13.83 | 17.12 | 144.97 |
| II | 13.09 | 4.66 | 137.26 |
| III | 13.62 | 7.49 | 142.83 |
| Average | 13.52 | 2.81 | 141.69 |

The PER dissolved in the lipid formulation is active; the fact that the activity of formulated protein is higher than of the reference standard (i.e. recovery>100%) may be due to a "protection" of the enzyme by the lipids against the negative effects of the organic solvents used to dissolve the formulation and standard samples.

Example 7

Preparation of Liquid Non-Aqueous Lipid Formulations of Pepsin (PEP) Using Spray-Dried PEP/Trehalose Powder Liquid lipid formulations were prepared as described in Example 1.

Aqueous solutions of PEP (MW ca 35 kDa) were prepared by dissolving PEP in an aqueous solution containing the required amount of polyhydroxy-component (TRE) in glass vials. The final PEP concentration was 10 mg/mL. The resulting solution was spray-dried using a BÜCHI Mini spray-drier. The resulting powder comprising PEP/polyhydroxy-component in weight ratio of 1:2.5 was finely grounded using a spatula before addition to the lipid formulations.

The spray-dried powder was added to the lipid formulations such that the final PEP concentration in the formulations was 1 wt % followed by end-over-end rotation for 1 day. The resulting formulations were then visually assessed for homogeneity and transparency where a homogenous and transparent sample indicates complete PEP dissolution. The results are given in Table 8.

TABLE 8

Lipid/PEP/polyhydroxy-component formulations
(lipid composition as in Table 1)

| Lipid formulation # | PEP/TRE (wt:wt) | Homogenous and transparent formulation | PEP conc. (wt %) |
|---|---|---|---|
| 1 | 1:2.5 | YES | 1 |
| 2 | 1:2.5 | YES | 1 |
| 3 | 1:2.5 | YES | 1 |

It is clear from the results in Table 8 that the spray-dried PEP/TRE-powder exhibits a high solubility in the non-aqueous lipid matrix. Importantly, pure PEP could not be dissolved to any visually observable degree in any of the lipid formulations 1-3.

Example 8

In Vivo Performance of Liquid Non-Aqueous Lipid Formulation of Somatostatin (SOM)

A liquid lipid formulation comprising SPC/GDO/EtOH=44/44/12 wt % was prepared as described in Example 1.

A freeze-dried powder of SOM (MW ca 1.6 kDa) and TRE was prepared in the same way as in Example 4 giving a SOM (free base)-to-TRE weight ratio of 1:2.5.

The freeze-dried powder was added to the lipid formulation such that the final SOM (free base) concentration in the formulation was 2 wt % (ea 20 mg/mL) followed by end-over-end rotation for 1 day. The resulting formulation was homogenous and transparent and was subjected to filtration through a 0.22 μm Millipore® PES membrane filter. The final filter-sterilized formulation was then injected subcutaneously to rats (male Sprague-Dawley).

In the in vivo rat model the release of SOM was followed during 14 days. The formulations were administered subcutaneously between the scapulae by using a syringe (23G, 0.6 mm×25 mm). The SOM concentration in the rat plasma was quantified using a commercial ELISA kit (S-1164, Bachem/Peninsula Laboratories, LOQ=0.03 ng/mL). The dose was 20 mg/kg and dose volume was 1 mL/kg corresponding to a drag load of 2.0 wt % SUM (free base).

Figure 1:
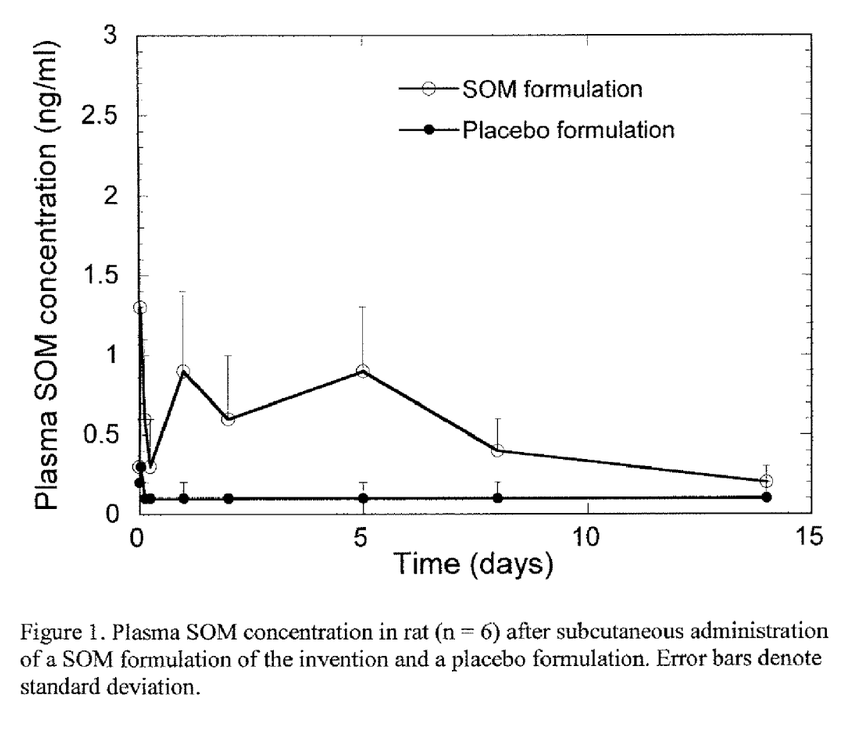
FIG. 1. shows plasma somatostatin concentration in rat (n=6) after subcutaneous administration of a somatostatin formulation of the invention and a placebo formulation. Error bars denote standard deviation.

From FIG. 1 (n=6) it is clear that the investigated formulation gives a release profile without a burst effect i.e. with a low initial release of SOM and with a $C_{max}/C_{14d}$=6.5. Furthermore, the SOM levels were higher (by a factor of 2-9 depending on time point) than the endogenous SOM levels over at least 14 days as can be deduced by comparing with the placebo formulation. It is noteworthy that despite the very short half-life of SOM in rat plasma (on the order of a few minutes) the formulation of the invention still provides at least 14 days duration.

The invention claimed is:

1. A formulation comprising:
   i) A lipid based controlled-release matrix comprising a low viscosity mixture of:
      a) at least one neutral diacyl lipid and/or a tocopherol;
      b) at least one phospholipid;
      c) at least one biocompatible, organic solvent comprising ethanol; and
      d) optionally at least one fragmentation agent;
   ii) a polyhydroxy component, wherein said polyhydroxy component is a disaccharide; and
   iii) a bioactive agent;
   wherein upon contact with aqueous media, following exposure to an aqueous environment, the formulation assembles into a bulk or particles of at least one ordered phase structure.

2. The formulation of claim 1, wherein the aqueous fluid is a body fluid.

3. The formulation of claim 1, wherein component a) is GDO, tocopherol, or mixtures thereof.

4. The formulation of claim 1, wherein component b) is phosphatidyl choline.

5. The formulation of claim 1, wherein the polyhydroxy component ii) is selected from the group consisting of trehalose, sucrose and mixtures thereof.

6. The formulation of claim 1, wherein the bioactive agent iii) is selected from the group consisting of interferons, glucagon-like peptide-1 receptor agonists, glucagon-like peptide-2 receptor agonists, somatostatin, somatostatin analogues and mixtures thereof.

* * * * *